United States Patent [19]

Renault

[11] 4,449,535
[45] May 22, 1984

[54] APPARATUS FOR MEASURING IN SITU THE STATE OF OXIDATION-REDUCTION OF A LIVING ORGAN

[75] Inventor: Guy Renault, Paris, France

[73] Assignee: Compagnie Industrielle des Lasers Cilas Alcatel, Marcoussis, France

[21] Appl. No.: 362,012

[22] Filed: Mar. 25, 1982

[30] Foreign Application Priority Data

Mar. 25, 1981 [FR] France .................. 81 05948
Feb. 12, 1982 [FR] France .................. 82 02323

[51] Int. Cl.³ .................. A61B 5/00; A61B 6/08
[52] U.S. Cl. .................. 128/634; 128/665; 350/96.29
[58] Field of Search .............. 128/633, 634, 664, 665, 128/397; 350/96.29

[56] References Cited

U.S. PATENT DOCUMENTS

| | | | |
|---|---|---|---|
| 3,136,310 | 6/1964 | Meltzer | 128/634 |
| 3,313,290 | 4/1967 | Chance et al. | 128/633 |
| 3,830,222 | 8/1974 | Chance | 128/665 |
| 3,867,033 | 2/1975 | Hasinger | 350/96.29 X |

OTHER PUBLICATIONS

Volz et al., IEEE Trans. on Biomed. Eng., vol. BME-26, No. 7, Jul. 1979, pp. 416-422.
Blumberg et al., Clinical Chemistry, vol. 23, No. 2, 1977, pp. 270-274.

Primary Examiner—Kyle L. Howell
Assistant Examiner—John C. Hanley
Attorney, Agent, or Firm—Sughrue, Mion, Zinn, Macpeak and Seas

[57] ABSTRACT

Apparatus having application to surgical operations has an ultra-violet laser pulse generator (1), an infrared laser pulse generator (3), an optical fibre (11) which transmits these pulses in one direction to the organ (13) and returns the fluorescence emitted by the organ together with reflected infrared radiation. Said returned radiation is detected by two receivers (25 and 20) and a circuit (31) for processing the electric signals delivered by said receivers.

13 Claims, 4 Drawing Figures

APPARATUS FOR MEASURING IN SITU THE STATE OF OXIDATION-REDUCTION OF A LIVING ORGAN

The present invention relates to apparatus for measuring in situ the oxidation-reduction state of a living organ.

BACKGROUND OF THE INVENTION

A known apparatus of this type is described in an article entitled "Optical consequences of blood substitution on tissue oxidation-reduction state microfluorometry" (by Shigeki Kobayashi et al) published in the United States magazine "Journal of applied physiology", vol 31, No 1, June, 1971. Said apparatus uses a radiation source which includes a mercury vapour lamp and filters. Said source is capable of illuminating an organ at two different wavelengths—an ultraviolet wavelength (366 nm) and a red wavelength (720 nm). Illuminating an organ at an ultraviolet wavelength causes fluorescence (at 440 to 480 nm) which is picked up by a photoelectric receiver.

The organ reflects part of the incident red energy in a reflected beam which is picked up by another photoelectric receiver. Said apparatus further includes a system for recording the output signals of the two receivers.

The measured intensity of the fluorescence is representative of the oxidation-reduction state of the organ.

However, variation in intra-tissue concentrations of red blood corpuscles disturbs the photometric measurements, in particular when experiments are made in situ in a living organ. It particular, a reduction of said concentration of red blood corpuscles causes an increase in the fluorescence recorded.

The variations in intensity of the reflected red radiation are representative of the intra-tissue concentration of red blood corpuscles.

By operating on an organ kept at a constant oxidation reduction state, by means of the apparatus described in said article, Kobayashi was able to draw graphs and to establish an equation relating fluorescence intensity to red reflection intensity obtained firstly on an organ emptied of its blood and secondly on an organ which contained varying quantities of red blood corpuscles. Kobayashi considers that the results obtained during his study show that it is possible to electronically compensate the variations in fluorescence as a function of the intra-tissue concentration of red blood corpuscles.

The apparatus described in said article therefore allows the NADH/NAD ratio to be studied over full, slow and provoked variations during experiments which can only be carried out in a laboratory on an isolated and artificially perfused organ separated from the system to which it belongs and therefore on a model which is far removed from its physiological state.

Preferred embodiments of the present invention provided apparatus for studying low-amplitude variations which are rapid (especially during a single cardiac cycle), spontaneous and/or provoked of the NADH/NAD ratio on an organ which is not separated from the system to which it belongs, said organ being normally perfused with blood in a physiological situation, in particular by simple tapping intravascular catheterization or endoscopic examination, said apparatus being designed for clinical applications, in particular during surgical operations.

SUMMARY OF THE INVENTION

The present invention provides apparatus for measuring the oxidation-reduction state of a living organ in situ, said apparatus having:

means for illuminating the organ with ultra-violet radiation and with radiation at another wavelength;

a first photoelectric receiver disposed to detect the fluorescence emitted by the organ in response to illumination by the ultraviolet radiation; and a second photoelectric receiver disposed to detect the beam reflected by the organ in response to illumination by said radiation at another wavelength;

wherein the means for illumining the organ include:

a first laser generator capable of emitting pulses of ultraviolet radiation;

a second laser generator capable of emitting pulses of radiation at said other wavelength;

means for concentrating said pulses of both wavelengths onto a single point; and a single optical fibre having a first end disposed in said organ and a second end disposed at said single point so as to:

convey said pulses in one direction from the second end to the first end so as to illuminate said organ; and convey in the opposite direction firstly the fluorescence emitted by the organ in response to illumination by the ultraviolet pulses and secondly part of the other radiation reflected by the organ in response to illumination by the pulses at said other wavelength.

BRIEF DESCRIPTION OF THE DRAWINGS

An embodiment of the present invention is described hereinbelow by way of example with reference to the accompanying drawings in which.

DETAILED DESCRIPTION

Figure 1:
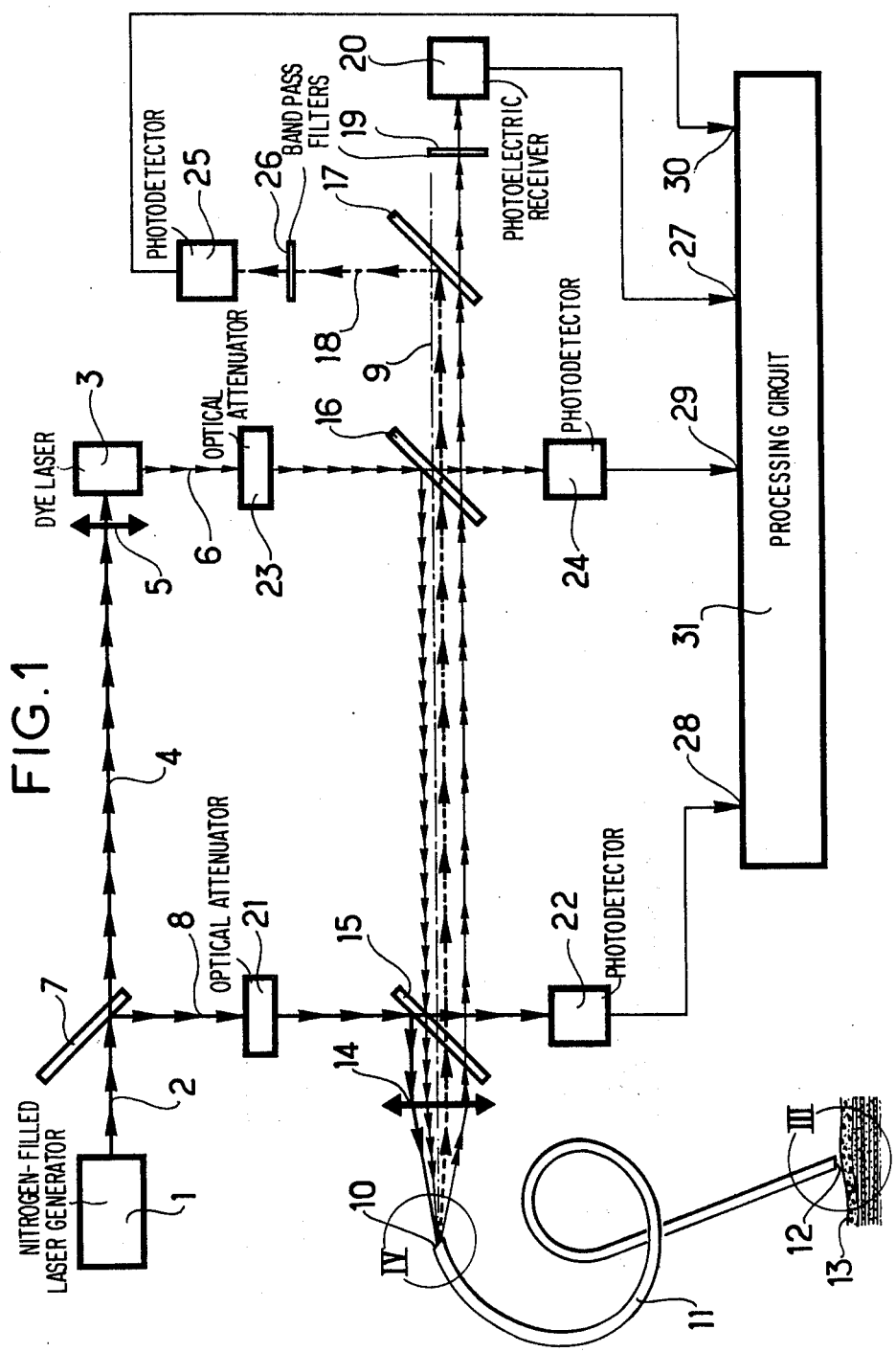
FIG. 1 is a schematic diagram of an embodiment of the apparatus in accordance with the invention.

In FIG. 1, a nitrogen-filled laser generator 1 emits an ultra-violet pulse 2 whose wavelength is 337 nm along an axis 4 towards the tank of a dye laser 3. The nitrogen-filled laser 1 is, for example, excited by a current wave which propagates along a flat excitation line, said wave being generated by an electric discharge across a spark gap. The dye laser 3 has a tank filled with a liquid constituted for example by a mixture of two dyes in a solvent, the two dyes being diethyloxatricarbocyanine iodide (DOTC) and hexamethylindotricarbocyanine iodide (HITC) and the solvent being dimethylsulfoxide (DMSO). Said tank is provided with a two mirror optical resonant cavity so as to be able to emit an infrared pulse with a wavelength of 805 nm along an axis 6 perpendicular to the axis 4.

An optical plate 7 is disposed at the output of the laser 1 and is inclined at 45° relative to the axis 4. Said plate reflects along an axis 8 ten percent of the energy of the pulse 2 at 90° and allows 90 percent of the energy of said pulse pass along the axis 4 towards a cylindrical converging lens 5 disposed between the plate 7 and the laser 3.

There are successively disposed along an axis 9 parallel to the axis 4:
- an end surface 10 of an optical fibre 11 whose other end surface 12 is disposed in a living organ 13;
- a converging lens 14 centred on the axis 9 with one of its foci situated on said end surface 10;
- an optical plate 15 disposed substantially at the intersection between the axes 8 and 9 and inclined at 45° to the axis 9 and perpendicularly to the plate 7;
- an optical plate 16 disposed substantially at the intersection between the axes 6 and 9 and parallel to the plate 16;
- an optical plate 17 disposed parallel to the plate 16 substantially at the intersection between a reflection axis 18 and the axis 9;
- an optical filter 19 disposed perpendicularly to the axis 9; and
- a photoelectric receiver 20.

On the axis 8, an optical attenuator 21 can be disposed between the plates 7 and 15 and a photoelectric receiver 22 can be situated beyond the plate 15.

Likewise, on the axis 6, an optical attenuator 23 can be disposed between the laser 3 and the plate 16 and a photoelectric receiver 24 can be situated beyond the plate 16.

The are disposed on the axis 18 a photoelectric receiver 25 and a filter 26 situated between the plate 17 and the photodetector 25.

There electric outputs of the four photodetectors 20, 22, 24 and 25 are connected to four inputs 27, 28, 29 and 30 respectively of a processing circuit 31.

Figure 2:
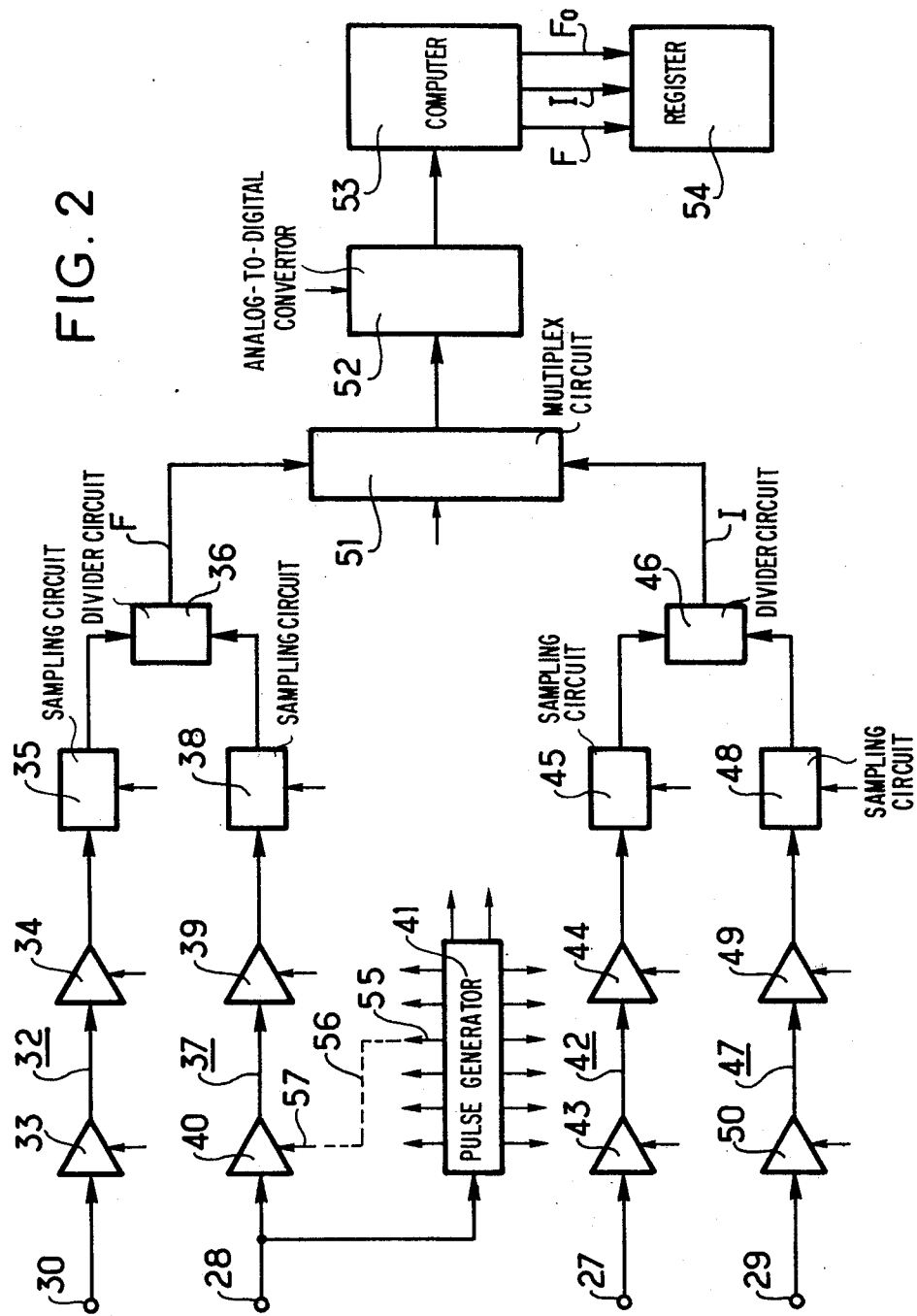
FIG. 2 is a block diagram of an electronic circuit which forms part of the apparatus illustrated in FIG. 1.

FIG. 2 is a block diagram of the processing circuit 31 in which diagram one end of a first branch circuit 32 is connected to the input 30 of the processing circuit. The first branch circuit 32 has, going from the input 30, an amplifier 33, an integrator 34 and a sampling circuit 35 all connected in series. The other end of the branch circuit 32 is connected to a first input of a divider circuit 36. A second branch circuit 37 connects the input 28 to a second input to the divider circuit 36 via an amplifier 40, an integrator 39 and a sampling circuit 38, all connected in series. A pulse generator 41 is connected to the second branch circuit 37 between the input 28 and the amplifier 40.

One end of a third branch circuit 42 is connected to the input 27 of the processing circuit. The branch circuit 42 has, going from the input 27, an amplifier 43, an integrator 44 and a sampling circuit 45 all connected in series. The other end of the branch circuit is connected to a first input of a divider circuit 46. A fourth branch circuit 47 connects the input 29 to a second input of the divider circuit 46 via an amplifier 50, an integrator 49 and a sampling circuit 48 all connected in series.

The outputs of the two divider circuits 36 and 46 are connected to respective inputs of a multiplex circuit 51 whose output is connected to the input of an analog-to-digital converter 52. The output of the converter 52 is connected to the input of a computer 53 whose outputs are connected to the inputs of a register 54.

The apparatus described hereinabove and illustrated in FIGS. 1 and 2 operates as follows.

Firstly, the nitrogen-filled laser 1 triggers an ultra-violet pulse 2 whose wavelength is 337 nm.

The plate 7 reflects 10% of the energy of said pulse along the axis 8 towards the plate 15 which reflects part of the energy of the pulse whose wavelength is 337 nm and allows the remainder of said energy to pass towards the photoelectric receiver 22. The ultra-violet pulse coming from the plate 7 and is therefore reflected parallel to the axis 9 by the plate 15 to be concentrated on the surface 10 of the fibre 11 by means of the lens 14.

The plate 7 transmits 90% of the energy of the pulse 2 along the axis 4. The energy thus transmitted is concentrated by the cylindrical lens 5 in the tank of the dye laser 3 so as to excite it. The laser 3 then emits an infrared pulse whose wavelength is 805 nm along the axis 6. The plate 16 is a partially reflecting plate at the wavelength of 805 nm; it reflects half the energy of the pulse coming from the laser 3 along the axis 9 and allows the other half of said energy to pass towards the photoelectric receiver 24. The plate 15 is transparent to light whose wavelength is 805 nm. It therefore allows the pulse which is reflected by the plate 16 to pass towards the lens 14 which concentrates said pulse onto the surface 10 of the fibre 11.

Practically, it can be considered that both the ultra-violet pulse and the infrared pulse reach the surface 10 at substantially the same instant.

By way of indication, the optical fibre may have a silica core with a diameter of 400 microns surrounded by an optical cladding also made of silica but having a lower refractive index. The optical cladding may have an outer diameter of 500 microns and itself be surrounded by a protective plastics covering with an outer diameter of 700 microns. Said plastics substance is sterilizable and is chosen from among those which have no coagulating effect on any blood which may come into contact therewith. Of course, if need be, such an optical fibre can be inserted in a catheter or the needle of a hypodermic syringe.

The optical fibre 11 transmits both the ultra-violet and the infrared pulses from the surface 10 to the surface 12 so as to illuminate the organ 13 which may be the heart of a patient being operated on, for example.

The ultra-violet pulse causes blue fluorescence in the organ 13 with an average wavelength of 480 nm which is transmitted by the fibre 11 from the surface 12 to the surface 10. Then said pulse is directed by the lens 14 along the axis 9, passing successively through the plates 15 and 16 which are transparent to blue light whose wavelength is around 480 nm.

The plate 17 reflects said blue light along the axis 18 towards the receiver 25 via the filter 26 which is a band-pass filter transmitting only the fluorescence.

Part of the energy of the infrared pulse transmitted to the organ 13 via the fibre 11 is reflected by said organ and transmitted in the opposite direction via the fibre 11 from the surface 12 to the surface 10. The lens 14 then directs the reflected infrared pulse along the axis 9 and said pulse passes through the plate 15 which is transparent to infrared radiation whose wavelength is 805 nm. Half the energy of said pulse passes through the plate 16 towards the plate 17 which is transparent to said radiation. The pulse is finally received on the receiver 20 after passing through the filter 19 which is a band-pass filter transmitting only the infrared radiation emitted by the laser 3.

The attenuators 21 and 23 are optical and serve to adjust the respective intensities of the ultra-violet and infrared pulses so as to match them to the various types of organ to be examined.

In the data-processing circuit, the divider circuit 36 calculates the ratio between the fluorescence signal and the ultra-violet emission signal from the laser 1 which signals are shaped in the branch circuits 32 and 37 respectively. A fluorescence signal F is thus obtained at the output of the circuit 36 independent from the intensity of the original laser signal as measured by the receiver 22.

Likewise, the divider circuit 46 calculates the ratio between the infrared reflection signal and the emission signal from the laser 3, these signals being shaped in the branch circuits 42 and 47 respectively. An infrared reflection signal I is thus obtained at the output of the circuit 46 independent from the intensity of the original laser pulse as measured by the receiver 24.

After passing via circuits 51 and 52, the signals F and I enter the computer 53 which is capable of deducing a value Fo from the values F and I, which value Fo corresponds to the equation:

$$Io/I = 1 + K \ln = \log \text{ natural } (Fo/F)$$

where Io and Fo designate the values of I and F which can be obtained when the organ is completely emptied of its blood, K and Io being constants which can be determined by prior tests.

The value of Fo thus obtained is independent from the intra-tissue concentration of red blood corpuscles; it is representative of the oxidation reduction state of the organ in question.

By means of each laser pulse emitted by the laser 1, the pulse generator 41 opens operating windows of predetermined duration in the components of all four branch circuits 32, 37, 42 and 47 as well as in the components 51 and 52 of the circuit 31. For said purpose, the pulse generator 41 has fourteen outputs represented by arrows and each component concerned has a control input also represented by an arrow. Each output of the generator 41 is connected to a control input. Thus, an output 55 from the generator 41 is connected by a link 56 to a control input 57 of the amplifier 40. These pulses of predetermined duration allow each component to operate only during a short time interval whose limits straddle the instant of arrival of the pulse. This makes it possible to avoid recording interference signals and in particular the signals of the reflections of the laser pulses on the surface 10 of the optical fibre 11.

As stated with reference to FIG. 2, the register 54 makes it possible to register not only the signal Fo but also the signals I and F.

The apparatus described hereinabove has numerous advantages.

The high power delivered by the various types of ultra-violet laser which operate in pulses at a repetition frequency which, by way of indication, may lie between 20 and 120 Hz, makes it possible to obtain a high level of fluorescence while maintaining the average power of illumination on the examined organ at a low value. In these conditions, said illumination does not of its own accord cause any disturbance of the value to be measured (e.g. NADH/NAD ratio) in particular by thermal effect and a fortiori does not alter the examined tissue.

The repetition frequencies set forth hereinabove make it possible to deliver a sufficient number of pulses per cardiac cycle to obtain precision in the case of measurements on man (heart frequency at rest: 1.2 Hz) or on animals (rat's heart frequency: 5 Hz).

Although it is possible also to use excimer or exciplex lasers to obtain fluorescence, nitrogen lasers are preferably used whose emission wavelength (337 nm) is very close to the absorption peak of NADH. This makes it possible to increase the signal-to-noise ratio.

The use of a dye laser as a source of infrared radiation has two advantages. Firstly, said laser can be excited by part of the energy of the pulses emitted by the ultra-violet laser so as to obtain two quasi simultaneous measurement pulses—an ultra-violet pulse and an infrared pulse. Secondly, the dye laser can be tuned on a wavelength of 805 nm which is referred to as "isosbestic" with respect to haemoglobin, i.e. for said wavelength, the coefficient of reflection of the organ depends neither on its oxidation-reduction state nor on the oxygenation state of the blood which flows through it.

The response time of the electronic processing circuit is very short so as to perform all of the operations in an appreciably shorter time than that which separates two laser pulses.

Using a single optical fibre makes it possible to obtain sufficient flexibility to follow, for example, the vascular path of a catheter. Another advantage of the single fibre is that it has only one fibre-to-tissue interface—a disposition preferable to that in which the emission interface is distinct from the receiving interface, since the energy ratio between the received radiation and the emitted radiation is higher.

However, the use of a single optical fibre to convey both the transmitted pulses and the received pulses sets a problem since interference reflections of these pulses on the end surfaces of the fibre may cause erroneous measurements. The problem becomes even more tricky to solve when the transmitted pulses and the received pulses have the same wavelength as in the case for the infrared reference used in the apparatus illustrated in FIG. 1. Indeed, in this case, it is not possible to prevent interference reflections by filters at the receiver.

In accordance with one disposition of the invention not illustrated in the figures, the end of the fibre in contact with the organ has a rounded e.g. hemisperical shape so as to reduce Fresnel interference reflecions.

In accordance with another disposition of the invention, the ends of the fibre have plane surfaces; the angle formed between the normal to the output surface 12 of the fibre and the transmission axis of said fibre is subjected to the following condition: said angle must be sufficient for no part of the laser pulses conveyed by the fibre and reflected by the surface 12 to be returned by the fibre in the opposite direction i.e. from the surface 12 to the surface 10.

Figure 3:
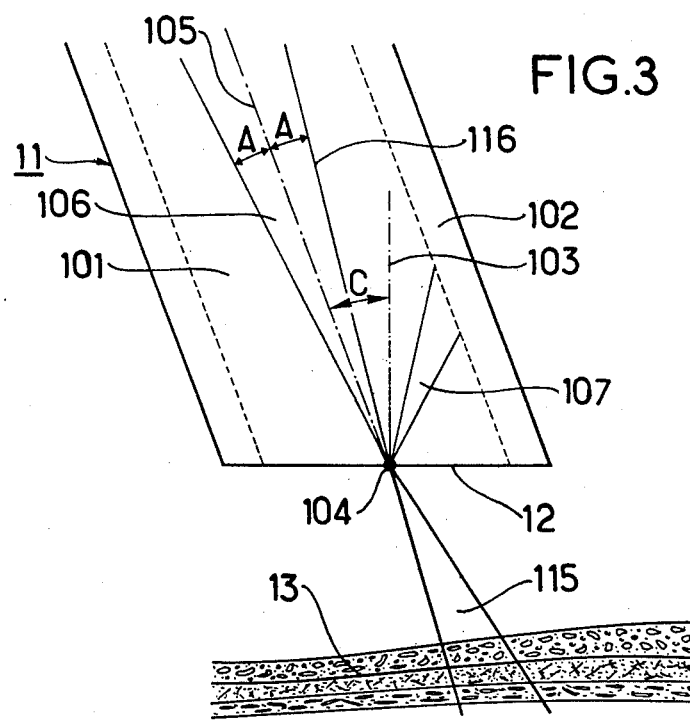
FIGS. 3 and 4 are two more detailed views, on a larger scale, of portions III and IV respectively of the apparatus illustrated in FIG. 1.

Said disposition is illustrated more clearly in FIG. 3. The case considered is that in which the fibre 11 has a core 101 with a refractive index $n_1$ surrounded by a cladding 102 with a refractive index $n_2$ which is lower than $n_1$. The normal 103 to a point 104 of the output surface 12 of the fibre forms an angle C with a transmission axis 105 of the fibre. The figure shows a conical laser beam 106 conveyed inside the fibre and concentrated on the point 104 of the surface 12 through which the greater part of the energy of the beam 106 passes to constitute an output beam 115 which illuminates the organ 13. The remainder of the energy of the beam 106 is reflected on the surface 12 to form a reflected beam 107. It is known that the rays of the beam 106 make narrower angles with the transmission axis 105 than the limit angle A for transmission along the fibre. The value of the angle A is given by the equation:

$$\cos A = n_2/n_1$$

In the position illustrated in FIG. 3, it is clear that all the rays of the reflected beam 107 are at an angle wider than A with the transmission axis 105: therefore all these rays are refracted and absorbed in the cladding 102 and cannot be transmitted in the opposite direction by the fibre towards the surface 10. This is true as long as the edge 116 of the beam 106 is on the same side of the normal 103 as is the axis 105. For the entire beam 107 to be refracted and absorbed in the cladding, we must therefore have:

C>A

The optical fibre 11 satisfies the above conditions.

Any interference reflections on the surface 12 due to the beams transmitted from the lasers 1 and 3 and conveyed by the fibre from the surface 10 to the surface 12 are therefore absorbed in the cladding of the fibre. Such interference cannot therefore be conveyed by the fibre in the opposite direction to return through the lens 14 and the plates 15 and 16 to be picked up by the receivers 20 and 25 and cause erroneous measurements.

By way of example, for a fibre made of doped silica and of pure silica whose respective refractive indices are $n_1 = 1.4585$ and $n_2 = 1.448$, the conditions C>A leads approximately to:

C>7°

A similar arangement can be made sloping the input surface 10 of the fibre relative to the axis of the laser pulses as concentrated by the lens 14. In this case the angle at which the pulses arrive must be sufficiently wide for that part of the radiation which is reflected on the input surface 10 to be reflected outside the lens 14.

Figure 4:
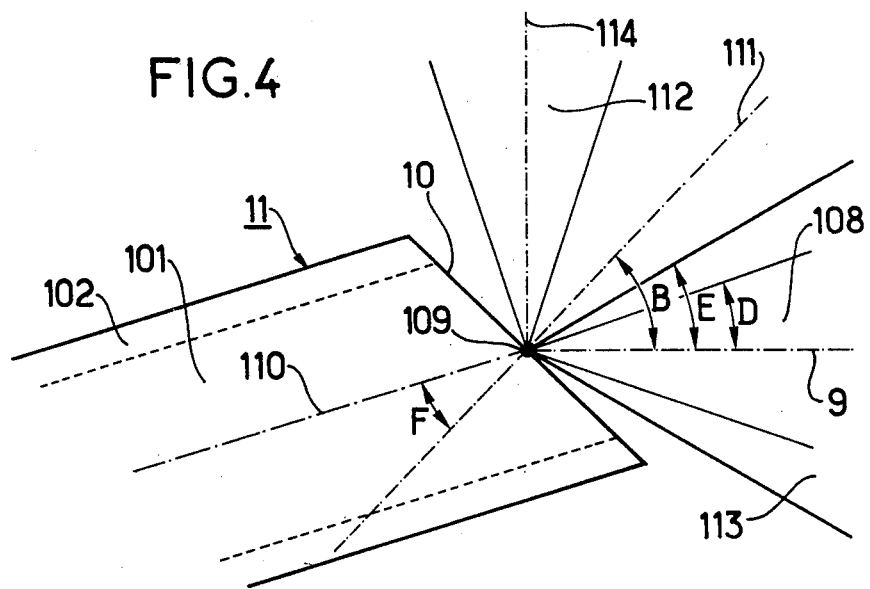

Said disposition is illustrated more clearly in FIG. 4. The fibre 11 has a core 101 with a refractive index of $n_1$ surrounded by a cladding 102 with a refractive index of $n_2 < n_1$. The figure shows the conical beam 108 leaving the lens 14 (FIG. 1) along the axis 9 and concentrated on a point 109 on the input surface 10 of the fibre 11. The point 109 is disposed on the transmission axis 110 of the fibre 11 and the axis 9 makes an angle of incidence B with the normal 111 to the surface 10. Part of the energy of the beam 108 is reflected by the surface 10 as a conical beam 112. To satisfy the previously set forth condition, the beam 112 must be situated completely outside a cone 113 whose apex is the point 109 and which rests on the edges of the lens 14.

Where E is the half-angle at the apex of the cone 113 and D is the half-angle at the apex of the cone 108, the equation is written as follows:

$B > E + D/2$

This disposition makes it possible to prevent interference reflections on the surface 10 from being picked up by the receivers 20 and 25 after passing through the lens 14 and the plates 15 and 16 in the opposite direction. It is possible to dispose an absorbent body in the average reflection direction 114 on the surface 10.

Of course, for the greatest possible proportion of laser energy to be transmitted effectively in the fibre through the surface 10, the radiation beam 108 which propagates along the axis 9 must be refracted in the core of the fibre in the direction of the transmission axis 110. Where F is the angle made by the axis 110 with the normal 111, we must have:

$n_3 \sin B = n_1 \sin F$ where $n_3$ is the refractive index of the surrounding medium.

By way of example, FIG. 4 shows an angle B of 45°. Where $n_1 = 1.4585$ and $n_3 = 1$, surrounding medium being air, the angle F is equal to about 29°.

Of course, without going beyond the scope of the invention, some technical means can be replaced by equivalent means.

Thus, the laser radiation whose reflection on the organ is used as a reference to measure the oxidation-reduction state can have any wavelength which does not interfere with the fluorescence wavelength, in which case the processing system 31 must have means to apply the corrections necessary to measure the oxidation-reduction state.

Preferably, said laser radiation has a wavelenth referred to as "isosbestic".

In particular, two isosbestic wavelengths are known: the infrared wavelength of 805 nm emitted by the dye laser 3 of the apparatus illustrated in FIG. 1 and an orange wavelength of 585 nm emitted by another dye laser.

The dye laser 3 used in the apparatus illustrated in FIG. 1 has the double advantage of emitting radiation at the isosbestic wavelength of 805 nm and of being excitable by the ultra-violet laser 1.

Further, it should be observed that it is possible in the configuration of FIG. 1 to dispense with the photoelectric receivers 22 and 24 as well as with the the attenuators 21 and 23 depending on the extent to which the lasers 1 and 3 deliver stable-power pulses for a given specific measurement.

The apparatus in accordance with the present invention can be used to continuously measure in situ the instaneous NADH/NAD ratio.

Said apparatus can be applied more especially to studying cardiac metabolism and in particular to studying the variations of said metabolism in pathology and during heart surgery. Cardiac metabolism can then be studied with respect to the endocardium, i.e. inside the heart cavities, by means of a catheter, firstly at the periphery and relating to either the veins or the arteries.

It can also be applied to studying other organs such as the brain, the liver and the kidney for example during pharmacological treatment or during the transformation of tumors.

I claim:
1. In an apparatus for measuring the oxidation-reduction state of a living organ in situ, said apparatus having:
   means for illuminating the organ with ultra-violet radiation and with radiation at another wavelength;
   a first photoelectric receiver means for detecting the intensity of fluorescence emitted by the organ in response to illumination by the ultra-violet radiation; and issuing an electric signal corresponding to the intensity of fluorescence and
   a second photoelectric receiver means for detecting the intensity of beam reflected by the organ in response to illumination by said radiation at another wavelength; and issuing an electric signal corresponding to the intensity of said reflected beam and
   wherein the means for illuminating the organ include:
   a first laser generator adapted to limit pulses of ultra-violet radiation;

a second laser generator adapted to emit pulses of radiation at said other wavelength;

means for concentrating said pulses of both wavelengths onto a single point; and a single optical fibre having a core with a transmission axis, a cladding surrounding said core which has a lower refractive index than said core said fiber further having a first end adapted to be disposed in said organ and a second end disposed at said single point so as to:

convey said pulses in one direction from the second end to the first end for illuminating said organ; and convey in the opposite direction firstly the fluorescence emitted by the organ in response to illumination by the ultra-violet pulses and secondly part of the other radiation reflected by the organ in response to illumination by the pulses at said other wavelength and processor means for calculating the oxygen-reduction state of the organ from the signals from said first and second photoelectric receivers, the improvement wherein;

the first and second ends of the fibre have a first plane end surface and a second plane end surface respectively, said first plane surface having a normal forming an angle with the transmission axis that is greater than the limit angle of the fibre.

2. Apparatus according to claim 1, wherein the second laser generator emits infrared radition pulses which constitute the radiation at said other wavelength.

3. Apparatus according to claim 1, wherein the first laser generator is a nitrogen laser generator.

4. Apparatus according to claim 1, wherein the second laser generator has an active medium constituted by a dye positioned to be excited by pulses emitted by the first laser generator.

5. Apparatus according to claim 4, wherein the excited dye emits pulses with a wavelength of 805 nm.

6. Apparatus according to claim 4, further including:
a third photoelectric receiver disposed to detect the pulses emitted by the first laser generator; and
a fourth photoelectric receiver disposed to detect the pulses emitted by the second laser generator.

7. Apparatus according to claim 6, wherein said means for concentrating the pulses of the radiation at both wavelengths on said single point comprise:
an optical system having a first optical axis defined by a line between said second photoelectric receiver and said point, a second axis defined by a line between said second laser generator and said fourth photoelectric receiver, said second axis being perpendicular to and crossing said first axis, and a first optical plate is positioned at the intersection of said first and second axes,
a third axis defined by a line between said first and second laser generators, and a second optical plate positioned on said third axis between said first and second laser generators, said third axis being parallel to said first axis and perpendicular to said second axis,
a fourth axis defined by a line between said second plate and said third photoelectric generator, said fourth axis being parallel to said second axis and being perpendicular to and crossing said first axis between said point and said first optical plate,
and a lens positioned on said first axis between said point and said third plate,
wherein said second optical plate is adapted to partially transmit ultra-violet light from said first laser along said third axis to excite said second laser, and to partially reflect ultra-violet light from said first laser along said fourth axis toward said third plate,
and said first optical plate is adapted to partially transmit light from said second laser to said fourth photodetector, to partially reflect light from said second laser toward said point along said first axis, and to transmit light received from the organ along said first axis toward said second photoelectric receiver,
and said third optical plate is adapted to partially transmit light reflected from said second plate toward said third photodetector and partially reflect light received from said second plate toward said point, and to transmit light received from the organ along said first axis toward said second photoelectric receiver.

8. Apparatus according to claim 7, further including:
a first ultra-violet radiation optical attenuator disposed on the fourth axis between the second and third optical plates; and
a second optical attenuator disposed on the second axis between the second laser generator and the first optical plate.

9. The apparatus according to claim 7, further including a fourth optical plate positioned on said first optical axis between said first optical plate and said second photoelectric receiver, said fourth optical plate being adapted to transmit light of the wavelength of the second laser toward said second photoelectric receiver and reflect fluorescence light generated in said organ toward said first photodetector.

10. Apparatus according to claim 6, wherein the processing circuit comprises:
first divider means for measuring the ratio between the amplitude of the signals from the first and third receivers respectively;
second divider means for measuring the ratio between the amplitude of the signals coming from the second and fourth receivers respectively;
a computer including means for correcting signals delivered by the first divider means in compliance with a predetermined law as a function of the signals delivered by the second divider means so as to obtain a compensated signal; and
a system for recording said signals.

11. Apparatus according to claim 1, wherein said concentration means has an optical system disposed to form a concentration beam centered around an axis of concentration, said single point being situated on the second end surface, the axis of concentration making a sufficiently wide angle of incidence with the normal to the second end surface for the part of the concentration beam reflected by the second end surface to be situated outside the optical system.

12. Apparatus according to claim 11, wherein the beam which propagates along the concentration axis is refracted in the fibre along the transmission axis of the fibre.

13. Apparatus according to claim 1, wherein said other radiation is at the isosbestic wavelength of 585 nm.

* * * * *